(12) United States Patent
Madding et al.

(10) Patent No.: US 6,845,913 B2
(45) Date of Patent: *Jan. 25, 2005

(54) METHOD AND APPARATUS FOR BARCODE SELECTION OF THEMOGRAPHIC SURVEY IMAGES

(75) Inventors: Robert P. Madding, Westford, MA (US); Bruce A. Poirier, Salem, NH (US)

(73) Assignee: Flir Systems, Inc., Billerica, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 350 days.

(21) Appl. No.: 09/248,419

(22) Filed: Feb. 11, 1999

(65) Prior Publication Data

US 2001/0045463 A1 Nov. 29, 2001

(51) Int. Cl.[7] .................................................. G06K 7/10
(52) U.S. Cl. .................................. 235/462.13; 235/375
(58) Field of Search ................................ 235/375, 385, 235/435, 439, 454, 462.01, 462.05, 462.13, 462.15; 156/277

(56) References Cited

U.S. PATENT DOCUMENTS

| | | | | |
|---|---|---|---|---|
| 4,396,942 A | * | 8/1983 | Gates ........................... | 358/107 |
| 4,520,504 A | | 5/1985 | Walker et al. .................. | 382/1 |
| 4,652,733 A | * | 3/1987 | Eng et al. ..................... | 235/462 |
| 4,890,244 A | | 12/1989 | Baggio et al. ......... | 364/551.01 |
| 5,219,226 A | | 6/1993 | James ........................ | 374/124 |
| 5,576,838 A | | 11/1996 | Renie ........................... | 386/117 |
| 5,576,950 A | * | 11/1996 | Tonomura et al. ........... | 364/514 |
| 5,580,172 A | * | 12/1996 | Bhardwaj et al. ........... | 374/137 |
| 5,602,377 A | * | 2/1997 | Beller et al. ................. | 235/462 |
| 5,635,012 A | * | 6/1997 | Belluci et al. ............... | 156/277 |
| 5,637,871 A | | 6/1997 | Piety et al. .................. | 250/330 |

(List continued on next page.)

FOREIGN PATENT DOCUMENTS

| | | | | |
|---|---|---|---|---|
| EP | 0 535 881 A1 | 4/1993 | .......... | G01N/25/72 |
| WO | WO 95/11454 | 4/1995 | .......... | G01N/33/50 |

*Primary Examiner*—Thien M. Le
*Assistant Examiner*—Jamara A. Franklin
(74) *Attorney, Agent, or Firm*—Invention Management Associates; Edward L. Kelley (57) ABSTRACT

The present invention provides a system and method for capturing video images of elements in a videographic survey, e.g. a thermograph video survey. According to the invention a barcode label having a bar pattern representing a unique identifying name of each element of the survey is associated with each survey element. A video camera system, with a barcode scanner associated therewith, is provided for scanning a barcode associated with a selected element. The selected element is thereby identified to the video camera system. The video camera system recalls data, including the element name, relating to the selected element and displays the data on a display device associated with the video camera system. An operator may review the displayed data and capture a video image of the element with the video camera system. The video image of the selected element may then be stored in a camera memory with the element name associated therewith. In another aspect of the invention, a base computer is provided, with a database program operating thereon, for organizing data fields, including an identifying name field, associated with each element of a survey. Data may be transferred between the video camera system and the base computer for organizing a videographic survey and for analyzing video images of the survey elements.

40 Claims, 9 Drawing Sheets

U.S. PATENT DOCUMENTS

| | | | | |
|---|---|---|---|---|
| 5,642,160 A | * | 6/1997 | Bennett | 235/380 |
| 5,675,149 A | * | 10/1997 | Wood et al. | 250/332 |
| 5,682,030 A | * | 10/1997 | Kubon | 235/462 |
| 5,729,252 A | * | 3/1998 | Fraser | 345/302 |
| 5,748,755 A | * | 5/1998 | Johnson et al. | 358/403 |
| 5,805,152 A | * | 9/1998 | Furusawa | 345/302 |
| 5,808,303 A | * | 9/1998 | Schlagheck et al. | 250/330 |
| 5,903,321 A | * | 5/1999 | Tung et al. | 348/715 |
| 5,903,706 A | * | 5/1999 | Wakabayashi et al. | 386/117 |
| 5,942,753 A | * | 8/1999 | Dell | 250/338.1 |
| 5,986,670 A | * | 11/1999 | Dries et al. | 345/629 |
| 6,015,088 A | * | 1/2000 | Parker et al. | 235/462.01 |

* cited by examiner

METHOD AND APPARATUS FOR BARCODE SELECTION OF THEMOGRAPHIC SURVEY IMAGES

FIELD OF THE INVENTION

The present invention relates in general to an infrared video camera system for use in thermographic inspection of equipment and for generating reports based thereon. In particular, the present invention provides a method and apparatus for storing a plurality of thermal images relating to a thermographic survey and for associating a barcode generated data field with a thermal image.

BACKGROUND OF THE INVENTION

Recent infrared (IR) video camera systems employing IR sensitive elements, e.g., a cooled or uncooled Charged Coupled Device (CCD) focal plane array, pyroelectric detector or the like, have been employed in infrared thermography systems for performing thermographic inspections or surveys of large numbers of elements. Thermographic images of an element may then be compared with a control image or other previously recorded thermographic image of the same scene or element. Such systems may be employed, e.g., in industrial facilities for plant maintenance, or the like, in which failures of electromechanical equipment, process equipment or other devices may be predicted based on abnormalities or "thermal events" detected in a live or recorded thermal image of the device being surveyed. Such thermographic surveys may also be employed in agricultural, medical, veterinary medical, law enforcement and military applications. In such applications, a thermographer may prepare a thermographic survey comprising a list of devices, objects or infrared scenes, called elements, to be recorded or surveyed. Each element is then periodically recorded using a thermographic video camera to record thermal video images of the elements of the survey. Thereafter, each video image of an element of the survey may be reviewed for comparison with a previously recorded control image of the element. By comparing the survey image with the control image, a thermal abnormality or thermal event may be detected. Such a thermal event may indicate a pending failure of the element. One such thermographic inspection system is disclosed by Piety et al. in U.S. Pat. No. 5,386,117.

Piety et al. disclose a mobile thermography system comprising an infrared camera, an ordinary visible image video camera, a personal computer, (PC), including an internal digital memory and a disk drive for digital data storage, a video recorder for recording analog video data, an LCD touch screen display device, a pen digitizer, various power storage devices, a system controller for operating various software which may be used to control and communicate between the various system elements, as well as, various other measuring devices, all mounted onto a mobile unit for ease of movement through a facility to be surveyed. Piety et al. also disclose a fixed base station computer including a digital data processor, for operating various digital data processing programs and including a video display and a printer for viewing video images, a memory, a disk drive, for digital data storage, an analog video recorder and analog video image processing equipment. In this case the mobile unit may be connected via communication ports with the base station computer at the beginning and end of each survey so that digital and or analog images, as well as, image identifying data may be communicated from the base unit to the mobile unit or from the mobile unit to the base unit as required.

According to Piety et al. software running on the base station computer is used to set up a framework of the thermographic survey. Such information as an element identifying name or control image, the type of element being surveyed, how to survey the element, fault types to look for, templates, notes, forms and the like are uploaded from the base station computer to the mobile unit prior to starting a survey to prompt the thermographic surveyor through the survey element by element and to record all information needed to generate a final report in the event a fault is discovered. After data collection is completed, the mobile unit is again connected to the base station computer and the collected survey images as well as other data which may have been entered by an operator during the survey are downloaded from the mobile unit to the base station computer for analysis and report generation.

One problem with this approach is that the thermographic surveyor is prompted through the thermographic survey in the predetermined order according to a survey route which is established by the original thermographic survey framework set up at the base station computer. In cases where the surveyor may wish to change the order or the route of the survey, the prompt information must be scrolled through in order to find the identifying information associated with a desired survey element. Since the survey may include many hundreds of images, this presents a problem to the surveyor when the order of the survey is changed. Another problem with the prior art approach is that many of the survey elements may be nearly identical, e.g. an electrical switch panel may contain tens or hundreds of substantially identical switches to be surveyed. In this case, an operator may confuse one switch with another. Even the element identifying information stored by the mobile unit may be confusing since element names and element control images may be very similar. For these reasons, an operator could easily loose the sequence of the survey thereby falsely identifying subsequent recordings.

A further disadvantage associated with the prior art is that occasionally a re-survey may be required to confirm or reevaluate a thermal event for one or a portion of the elements of the survey. By the prior art methods, a surveyor would be forced to scroll through the entire survey to reach the data associated with the element or elements to be resurveyed.

SUMMARY OF THE INVENTION

The present invention obviates the disadvantages associated with the use of a route based or predetermined videographic survey sequence or with the need to sequentially scroll through survey element data stored on a video camera used for a video survey or data collection with a video camera system by providing a barcode label associated with an element to be surveyed and a barcode scanner associated with the video camera system and by storing identifying information associated with each element of the survey in an a electronic memory associated with the video camera system.

Generally, the present invention provides an integrated video camera system for capturing a video image of an element. The camera system includes a digital data processor and a memory module in communication with the digital data processor for storing program steps and for storing digital data in data fields provided on the memory module. According to the present invention, a barcode including a bar pattern representative of an identifying name of the element is associated with the element and a barcode scanner, in communication with the digital data processor, is used to scan the barcode. The barcode scanner generates an electrical signal in response to scanning the barcode and the electrical signal is interpreted by the digital data processor to associate the identifying name of the element with an appropriate data field provided on the memory module. When a video image of the element is captured, the video image of the element is stored onto the memory module with the identifying name of the element associated therewith. The memory module may also include a first data field having the identifying name of the element stored therein and a second data field associated with the first data field for storing a video image of the element.

In order for an operator to view a video image of an element, the integrated video camera system may further comprise a video display device in communication with the digital data processor for viewing the video image of the element and for viewing the identifying name of the element. A keypad in communication with the digital data processor may also be included for providing an operator interface to the video camera system so that the operator may give commands to the camera, e.g. for scrolling between video images, or the like. The memory module may be formed by having an internal memory associated with the video camera system, e.g. a read only memory, (ROM), for storing the program steps and a separate removable memory module, e.g. a PCMCIA card installed in a PCMCIA slot on the video camera system, for storing the digital data relating to the element in data fields provided on the removable portion of the memory module.

The integrated video camera system may also be used for capturing a plurality video images of a plurality of elements included in a videographic survey. In this case, each of the plurality of elements has a unique identifying name and the memory module includes a plurality of data fields relating to each of the plurality of elements such that a separate data field is provided for storing each of the identifying names of the plurality of elements. In this case a barcode is provided associated with each of the plurality of elements such that upon scanning one of the bar-codes the electrical signal generated by the barcode scanner is interpreted by the digital data processor to associate the identifying name of the element associated with the barcode with an appropriate data field provided on the memory module. A video image of the element associated with the barcode is stored onto the memory module with the identifying name scanned from the one barcode associated therewith. In addition, upon scanning a barcode, the identifying name of the element associated with the barcode is determined by the data processor and a display screen having data fields relating to the element associated with the barcode may be displayed on the video display device.

Also according to the present invention there is provided a method for capturing a video image of an element with a video camera system which includes a digital data processor for executing program steps, a memory module in communication with the digital data processor for storing the program steps and for storing digital data in data fields and a barcode scanner in communication with the digital data processor. The method comprises the steps of, associating a barcode comprising a bar pattern representative of an identifying name of an element with the element, scanning the barcode with the barcode scanner thereby generating an electrical signal in response to scanning the barcode and interpreting the electrical signal according to the program steps to associate the identifying name of the element scanned from the bar pattern with an appropriate data field provided on the memory module. The method further includes the steps of capturing a video image of the element and storing the video image of the element onto the memory module in an image data field having the identifying name of the element associated therewith. The method may further include the steps of establishing a plurality of digital data fields on the memory module for storing digital data associated with the element, storing the identifying name of the element in one of the plurality of data fields and associating the identifying name of the element with all of the other of the plurality of digital data fields.

An operator may retrieve the image data field and the identifying name data field of the element from the memory and display a video image of the element and the identifying name of the element on a video display device associated with the video camera system. In some cases the video camera system may determine a plurality of parameters relating to the step of capturing the video image of the element and store the plurality of parameters in the plurality of data fields established on the memory module and associated with the identifying name of the element.

The method may also include the steps of storing the program steps in an internal memory associated with the video camera system while the step of storing the video image of the element on the memory module stores the video image onto a removable memory module, e.g. a PCMCIA card which is removable from the video camera system.

The method may also be used for capturing a plurality of video images of a plurality of elements included in a videographic survey in which case the steps include, associating a plurality of bar-codes with the plurality elements, each of the plurality of bar-codes having a bar pattern representative of the identifying name of the element associated with the barcode, scanning a first barcode associated with a first of the plurality of elements with the barcode scanner thereby generating an electrical signal in response to scanning the first barcode; and, interpreting the electrical signal to determine the identifying name scanned from the bar pattern of the first barcode to associate the identifying name of the first element with an appropriate data field on the memory module. As above, the method includes capturing a video image of the first element and storing the video image of the first element onto the memory module in an image data field having the identifying name of the first element associated therewith. In this case, further steps include establishing a plurality of digital data fields on the memory module for storing digital data associated with each of the plurality of elements of the survey, storing the identifying name of each of the plurality of elements of the survey in separate data fields of the plurality of data fields and associating the identifying name of each of the plurality of elements of the survey with a portion of the plurality of digital data fields such that each of the plurality of elements includes a plurality of data fields associated with the identifying name of the element. The method further includes the steps of retrieving the image data field having the identifying name of the first element associated therewith and displaying the video image of the first element and the identifying name of the first element on a video display device associated with the video camera system.

According to the present invention, there is also included a method for performing a videographic survey of a plurality of elements. The steps include preparing a videographic survey database on a base computer such that the videographic survey database includes a plurality of data fields for storing data associated with each of the plurality of elements. The database includes one data field for storing an identifying name for each of the plurality of elements and a data field for storing a video image of each of the plurality of elements and the data fields for storing the identifying name are each associated with an appropriate data field for storing a video image of each elements of the survey.

The base computer also includes a program for generating each of the identifying names in a barcode format. After establishing the database on the base computer the method includes the steps of transferring the data fields to a memory module associated with a video camera system and associating a plurality of bar-codes, one barcode with each of the plurality of elements. The base computer may also include a barcode label printer associated therewith for printing barcode patterns onto labels for associating a label with each of the plurality of elements of the survey.

Each of the plurality of bar-codes includes a bar pattern representative of the identifying name of the element associated with the barcode. According to the method, an operator scans a first of the plurality of bar-codes with a barcode scanner in communication with the video camera system to determine the identifying name of the element associated with the first barcode. The digital data processor associated with the camera system interprets the barcode signal to determine the identifying name of the element and then selects the appropriate data field of the database for storing a video image of the element associated with the first barcode. An operator may then capture a video image of the element associated with the first barcode with the video camera system and the digital data processor stores the video image of the element in the appropriate data field of the database associated with the identifying name of the element.

To complete the video survey, the method further includes the steps of scanning the remaining of the plurality of bar-codes with the barcode scanner, selecting the appropriate data field of the database for storing a video image of the remaining of the plurality of elements associated with the remaining of the plurality of bar-codes and capturing a video image of each of the remaining of the plurality of elements of the videographic survey and storing the video image of each of the remaining of the plurality of elements of the survey in the appropriate data field of the database such that the identifying name of the remaining of the plurality of elements is associated with the video image of remaining of the plurality of elements.

In the final steps of the method, the data fields stored on the memory module of the video camera system are transferred back to the base computer which may be used to analyze the videographic survey data using programs stored on the base computer or to store an archive of the videographic survey data onto a memory associated with the base computer using programs stored on the base computer. In addition, an operator may choose to scan less than the remaining of the plurality of bar-codes with the barcode scanner.

BRIEF DESCRIPTION OF THE DRAWINGS

The features of the present invention will best be understood from a detailed description of the invention and a preferred embodiment thereof selected for the purposes of illustration and shown in the accompanying drawing in which.

DETAILED DESCRIPTION OF THE INVENTION

Figure 1A:
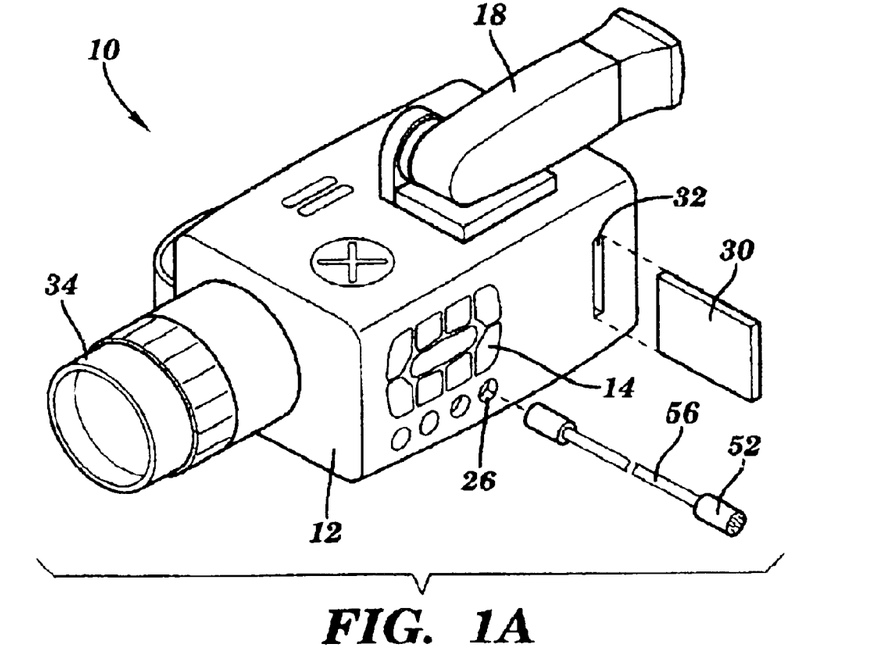
FIG. 1A illustrates a video camera system in accordance with a preferred embodiment of the present invention.
Figure 1B:
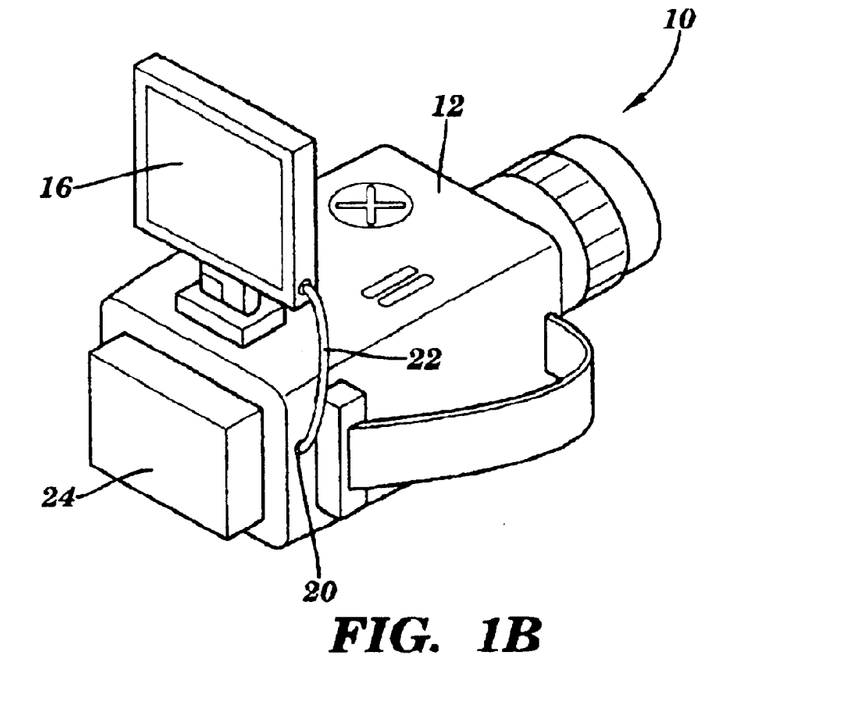
FIG. 1B illustrates another embodiment of a video camera system in accordance with a preferred embodiment of the present invention.

Referring now specifically to FIGS. 1A and 1B, there is illustrated an integrated infrared video camera system 10 for use in collecting thermographic survey data in accordance with a preferred embodiment of the present invention. The infrared camera system 10 generally includes a camera body 12, for housing a video camera image capturing system, a keypad or data entry device 14, for providing an operator interface to the infrared camera 10, and a color or gray scale video display device 16, which may be incorporated within the camera body and viewable through a viewfinder eyepiece 18, or, which may be optionally connected to the camera 10 via a separate display device port 20 by an appropriate interface connector 22. The display device 16 may comprise a liquid crystal display, (LCD), a cathode ray tube, (CRT), or any other display device for viewing thermal or other video images in real time, and/or for scrolling through and reviewing previously captured or stored thermal or other video images.

The camera 10 also includes a removable memory module 30 such as a PCMCIA memory card which installs into a memory module port 32 for communicating with the camera 10. Other removable or non-removable memory modules may also be used such as a disk drive, tape drive, or other magnetic memory component, or a recordable compact disk memory, CD, or other optical memory device, or other suitable internal or external electronic digital data storage devices or analog memory devices, such as a video cassette recorder, may be provided to store thermal images captured by the infrared camera 10.

The camera 10 also includes an imaging lens assembly 34 for relaying an image of a scene onto an imaging sensor for capturing an electronic image of the scene. The imaging lens assembly 34 may be interchangeable with other imaging lens assemblies having different optical properties, e.g. field of view or magnification. The lens assembly 34 may also include an optical filter, (not shown), for filtering out unwanted wavelengths emitted by the scene. The camera 10 may also include one or more input/output, (I/O), ports 26 for connecting other devices to the camera 10 such as a base computer, (PC), a portable computer or laptop, a printer, fax, or other communication device, an optical or thermal measurement instrument, diagnostic equipment, additional data storage devices, other display or data entry devices, an audio microphone, audio headphones or any other device which may aid the thermographer in capturing survey data.

Figure 2:
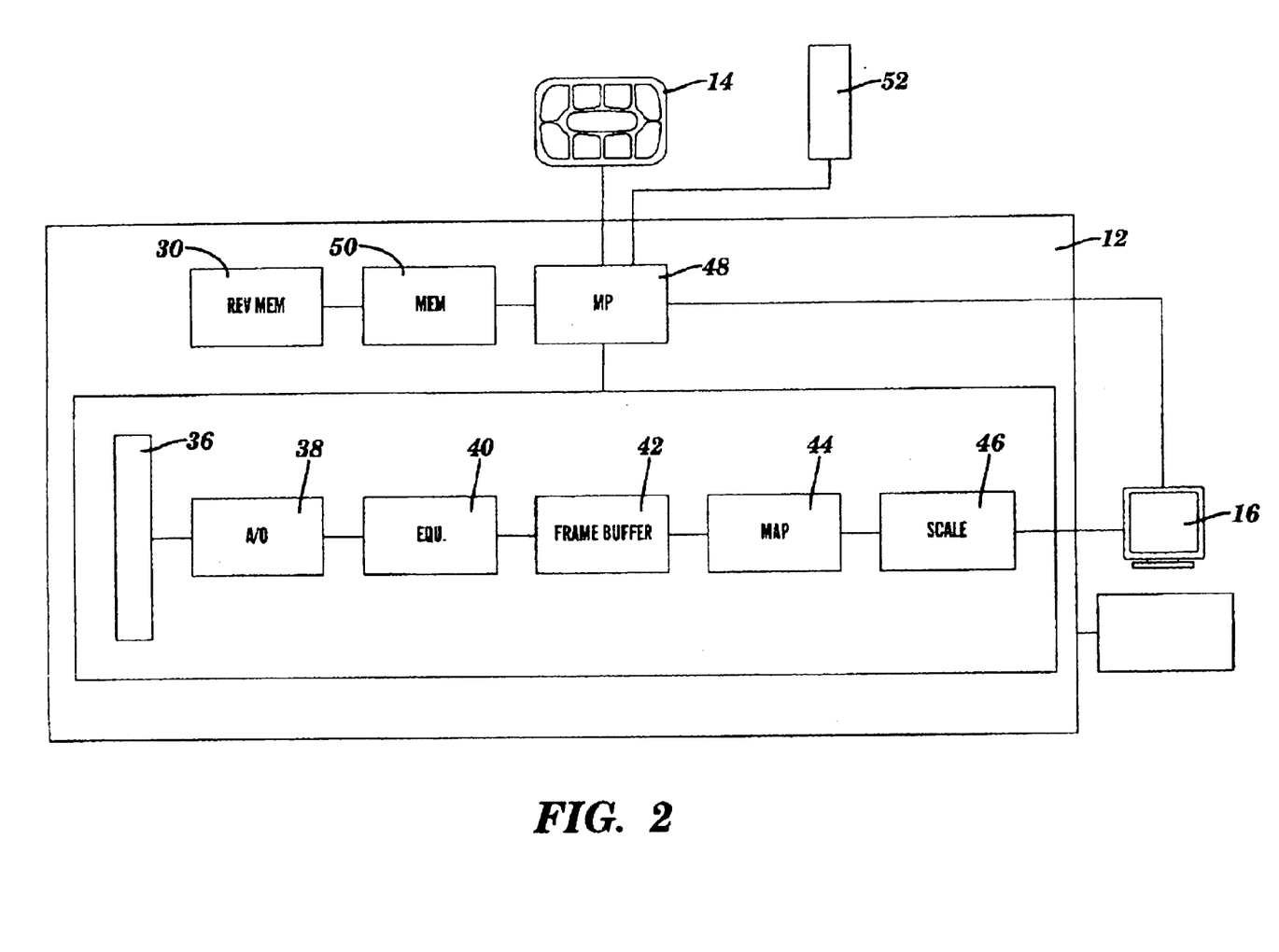
FIG. 2 illustrates a schematic overview of a video camera system in accordance with a preferred embodiment of the present invention.

Depicted schematically in FIG. 2, the camera 10 also includes an infrared sensor assembly 36, such as a cooled or uncooled focal plane array, e.g. a charged coupled device array, (CCD), or pyroelectric detector or array, or the like, for providing an electrical signal in response to receiving thermal radiation emitted by a scene under analysis thereon. Of course, other types of infrared sensors or scanners may also be used to detect the thermal profile of a scene without departing from the intended scope of the present invention. The sensor assembly 36 may also have sensitivity at the visible wavelengths so that a visible image of survey elements may also be captured. Additionally, more than one sensor assembly 36 may be employed such that an optical image from the lens 34 may be redirected by a mirror, or the like, to a second sensor assembly so that infrared and visible image data could be captured by different sensors installed in the same camera system 10. Alternatively, a separate visible image capture device may also interface with I/O ports 26 so that digital visible images may be captured by the separate visible wavelength video camera device and communicated to the camera 10 for storage on the memory module 30.

The analog output of the infrared sensor assembly 36 is converted into digital image data by an analog to digital, (A/D), converter 38. Thereafter, the digital image data produced by the A/D converter is directed into an equalization processor 40, which applies a pixel to pixel correction to the digital image data in a manner known in the art. The corrected digital image data is subsequently stored in a frame buffer 42. This same corrected digital image data may also be stored on the removable memory module 30. The digital image data is output from the frame buffer 42, mapped by a mapper 44 and scaled by a scaler 46, as necessary for displaying the corrected digital image of the scene, again in a manner known in the art, onto display device 16 of the infrared camera system 10. In addition, the corrected digital thermal image data and other information (see below) displayed on the display device 16 may be stored in the memory module 30 or in another storage device associated with the infrared camera 10 for immediate viewing, for later analysis or for archival purposes.

A microprocessor 48 controls the operation of the infrared camera 10 and the display device 16 in response to programmed instructions stored in an internal digital memory 50, e.g. a read only memory, (ROM), or programmable or flash memory or the like, and in response to operator commands input via the keypad 14. The microprocessor 48 may also process programmed instructions for displaying text and other graphic symbols onto the display device 16 such that text data fields may be displayed simultaneously with a video image or exclusively text and graphic images may be displayed on the display device 16. Such programmed instructions as well as data associated with survey elements may reside on the memory 50 or the memory module 30 or on another interconnected memory device such that the microprocessor 48 interacts with a memory and with keypad 14 to receive input instructions from an operator, receive data and/or programming instructions from the memory 30 or 50 and drive the display device 16 such that video images, text data fields and other graphical images are displayed to the operator.

Figure 3A:
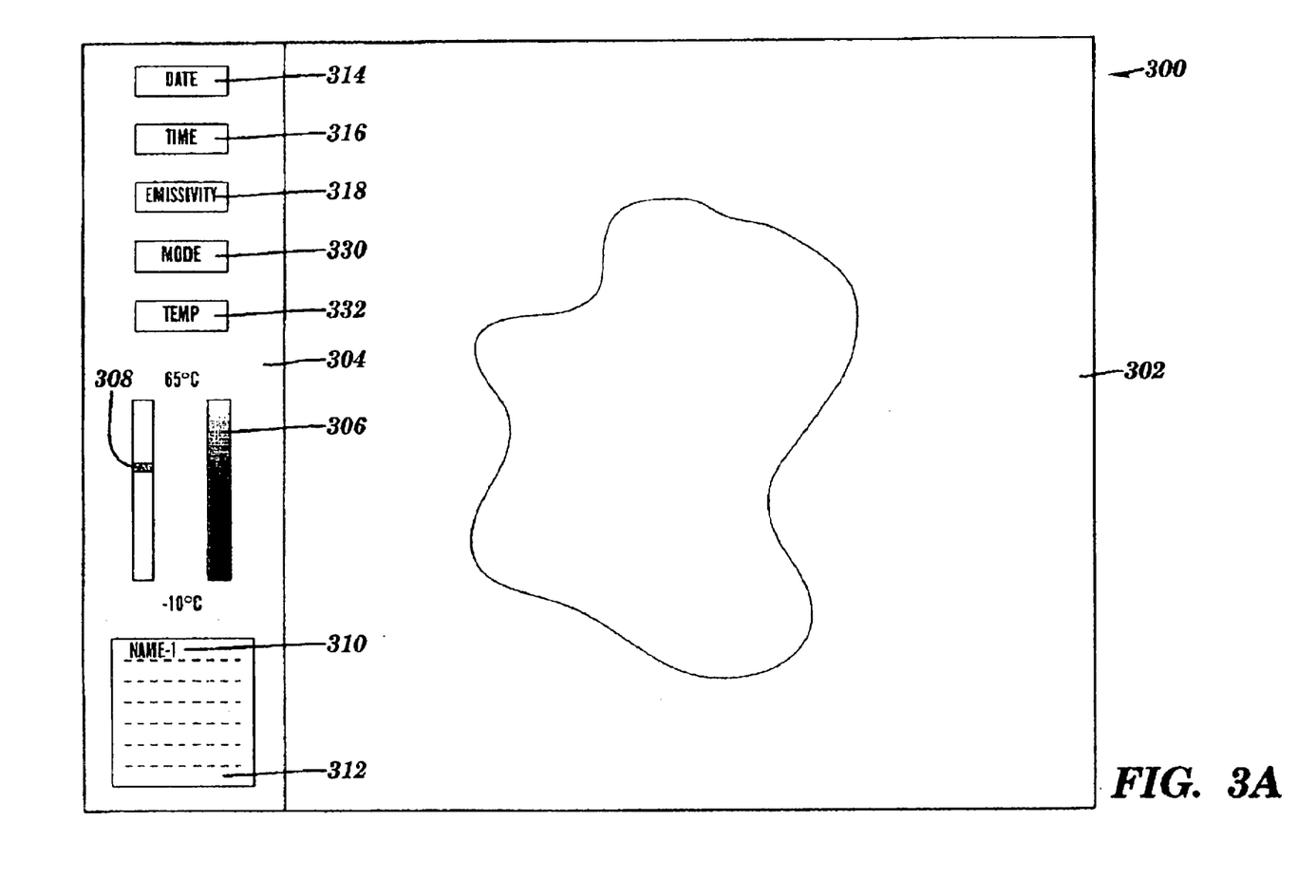
FIG. 3A illustrates a single survey element display screen in accordance with a preferred embodiment of the present invention.
Figure 3B:
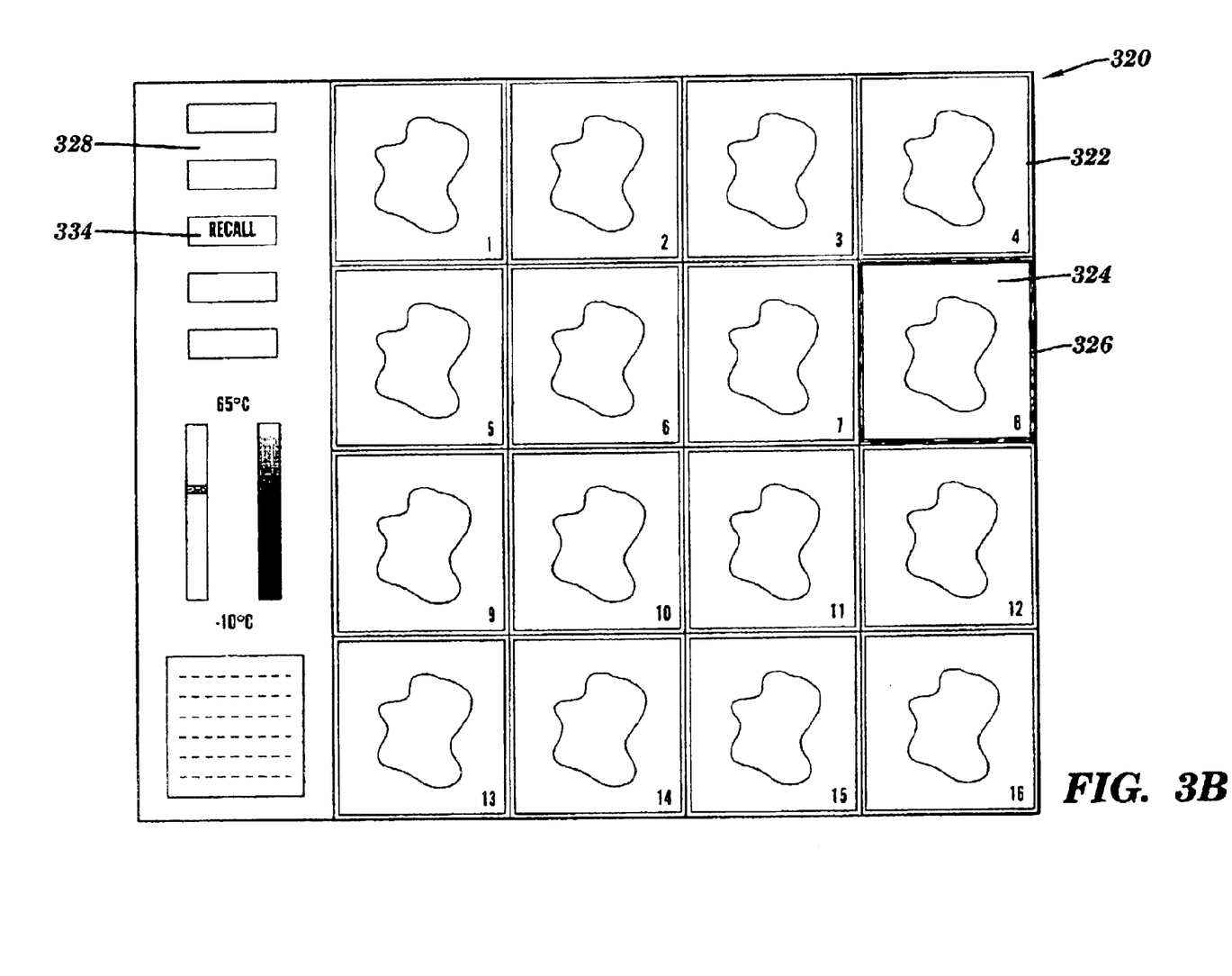
FIG. 3B illustrates a thumbnail display screen in accordance with a preferred embodiment of the present invention.

Camera display screen views are illustrated in FIGS. 3A and 3B. In FIG. 3A a single survey element screen 300 is displayed. An image display area 302 displays a live or captured thermographic or visible image of the survey element. An information panel 304 displays data fields relating to the image display area 302, e.g. a recording date and time are constantly displayed in a data fields 314 and 316, an object emmissivity in field 318, a camera mode in field 330, a temperature of a selected point of the image area 302 in field 332 and a range of temperatures of the scene displayed in area 302 which is displayed graphically by range indicators 306 and 308. An element identifying field 310 is displayed in a scrolling information window 312. Field 310 contains a unique identifying name, number or other identifying feature associated with the survey element. The identifying name displayed in field 310 is also associated with previously recorded images and/or data sets which relate to the particular survey element being viewed in the image area 302. Such previously recorded images and data which may be stored on the memory mode 30 or on a base computer which will be described below.

As illustrated in FIG. 3B, a thumbnail screen display 320 includes an image display area 322 which displays 16 thumbnail images 324. In this case one of the thumbnail images 324 is highlighted by an outline 326 surrounding the thumbnail image 324. A set of image data relating to the highlighted thumbnail image 324 is displayed by an information panel 328 which may include the same image information as is displayed in the information panel 304, detailed above, but which may also include a RECALL button 334 for selecting the highlighted thumbnail image 324 and viewing the highlighted image 324 in the single image view format of the above described display screen 300. An operator may scroll through the thumbnail images 324 using the keypad 14 which scrolls the highlight outline 326 from one image to the next while also refreshing the information panel 328 with the data associated with the highlighted thumbnail image 324.

Since a thermographic survey may include many more than 16 survey elements, once a first set of 16 thumbnails images has been scrolled through, a new set of the next 16 thumbnail images 324 is automatically loaded into the thumbnail display screen 320. In this case, a reference image, a visible image or no image but just the information panel 328 associated with each element of the survey may have been loaded onto the memory module 30 such that between 10 and 300 images are typically stored on the camera system 10 during a survey. Furthermore the operator may be required to identify 10 to 300 survey elements, match each survey element with a thumbnail images stored on the camera 10 and capture a new thermal image of the survey element. Since the thumbnail images are small and since many survey elements may look similar, an operator could easily associate a wrong thumbnail image with the survey element.

Figure 4A:
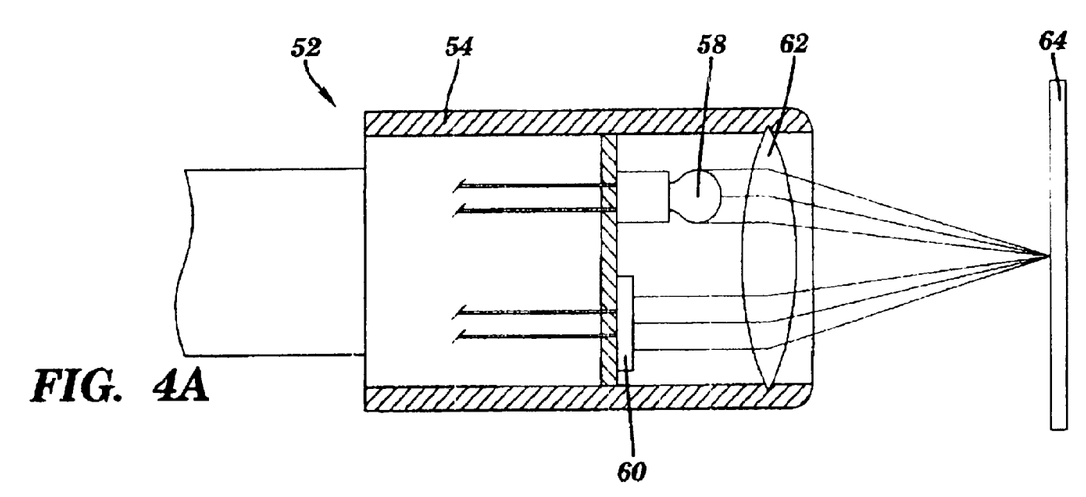
FIG. 4A illustrates a barcode scanner in accordance with a preferred embodiment of the present invention.

The camera 10 further includes a barcode scanning device, referred to generally by reference numeral 52 and connected to the camera 10 via one of the I/O ports 26 by a connecting wire 56. Such a barcode scanning device 52, shown in FIG. 4A, is well known in the art and may comprise a hand held casing 54, an illuminating light source 58, such as a light emitting diode, (LED), or the like, which receives power from the camera 10 via connecting wire 56 and is controlled by a barcode reader program stored in a memory 50 associated with the microprocessor 48.

Figure 4B:
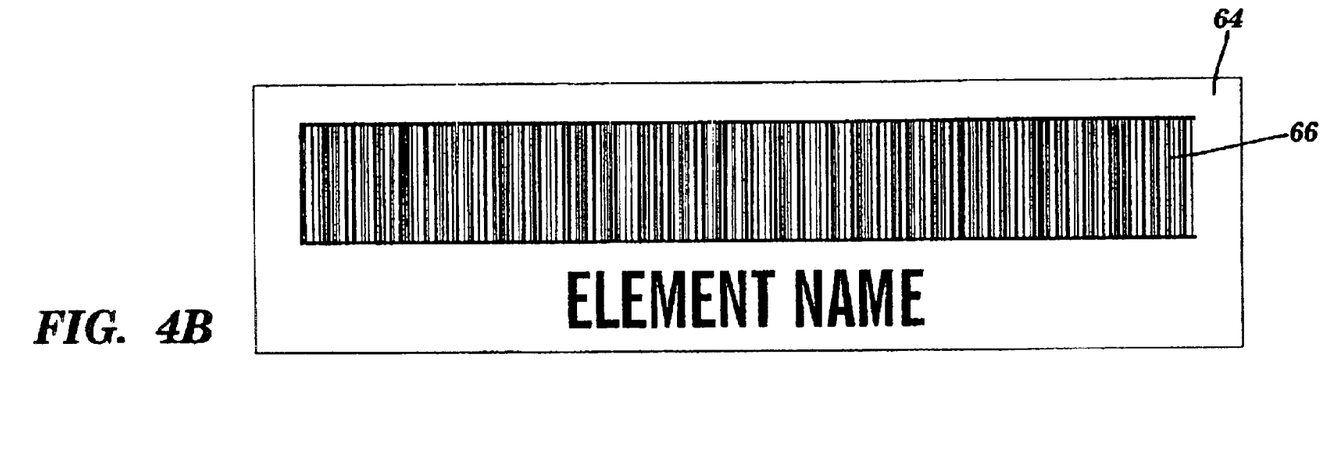
FIG. 4B illustrates a barcode label in accordance with a preferred embodiment of the present invention.

The barcode scanner 52 also includes a light sensitive detector or sensor 60 for providing an electrical signal in response to illumination falling thereon. Connecting wire 56 may also provide a voltage and or biasing current to the sensor 60 and communicates an electrical signal generated by the sensor 60 to the microprocessor 48 for analysis. A lens 62 may also be provided for focusing light from the illuminating light 58 onto a barcode label 64 and for collecting light reflected by the barcode label 64 and directing the reflected light from the barcode label onto the sensor 60. A barcode 66 recorded onto the barcode label 64 may include a plurality of bar patterns each representing an alpha-numeric character, or the like, as is well known.

Such a barcode label 64 which includes a barcode 66 may be attached to the survey element or otherwise associated with the survey elements. In this case, the barcode 66 represents a unique element identifying name such as the same name displayed in the display field 310 of the display screen 300 and 302.

In this way, an operator may scan a barcode 66 printed on a barcode label 64, which is attached to or otherwise associated with a survey element to be surveyed or recorded, by passing the hand held barcode scanner 52 over the barcode 66. As the barcode 66 is scanned, a series of electrical signals generated by the sensor 60 are communicated to the microprocessor 48 which interprets the electrical signals as alphanumeric characters using a barcode interpreting instruction set stored in the memory 50 and processed by the microprocessor 48. In this way, a unique survey element name, number or other alpha-numeric identifying feature is read from a barcode label 64 and communicated to the microprocessor 48. The microprocessor 48 may then search through the survey data stored on the memory module 30, or other interconnected memory device, to match the element identifying name of the barcode label with a particular survey data set and directly display the selected survey data in the manner shown in FIG. 3A.

This method speeds up the survey since an operator does not need to scroll through images or image data to find the appropriate survey element and it reduces errors which may occur when a wrong data set is associated with a survey element. Moreover, the method of the present invention allows survey elements to be surveyed in any order without causing undue delay or errors.

The camera system 10 may be used to capture video images, store the images onto the memory module 30, recall the images and view the images on the display device 16. Furthermore, thermographic survey data, including images, relating to a survey element may be loaded and stored on the memory module 30 so that an operator may also view previously recorded infrared or visible wavelength images of a survey element on the display device 16 by scrolling through images using the keypad 14 to input commands.

Furthermore, data and images relating to a survey element includes a unique identifying name which is stored as a data field 310 with the survey element data. The camera 10 may be used to scan a barcode label 66 associated with the survey element to recall the appropriate survey element data set by matching the name on the barcode label with the unique identifying name associated with the survey element data.

Figure 5A:
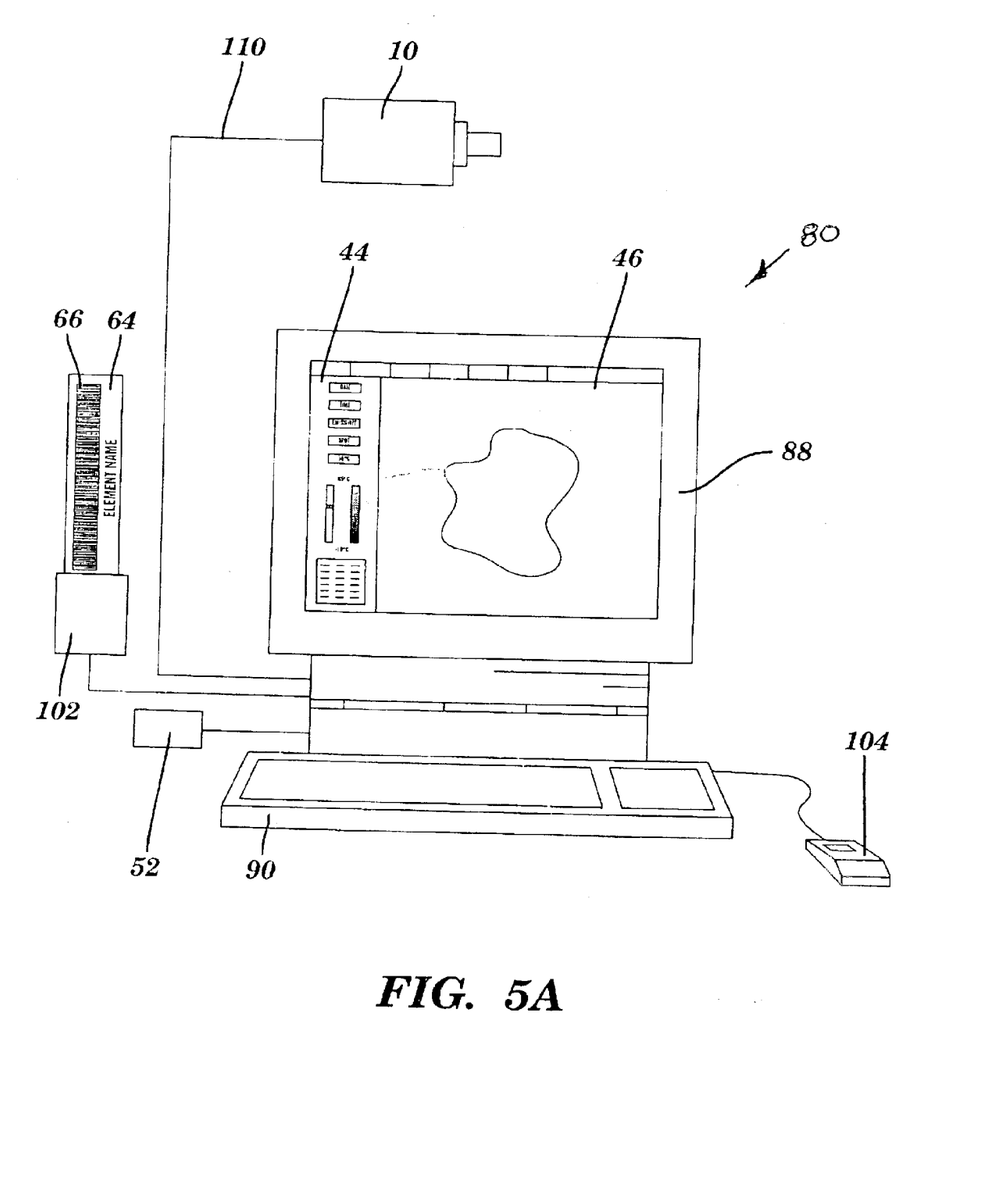
FIG. 5A illustrates a video camera system connected to a base computer system in accordance with a preferred embodiment of the present invention.
Figure 5B:
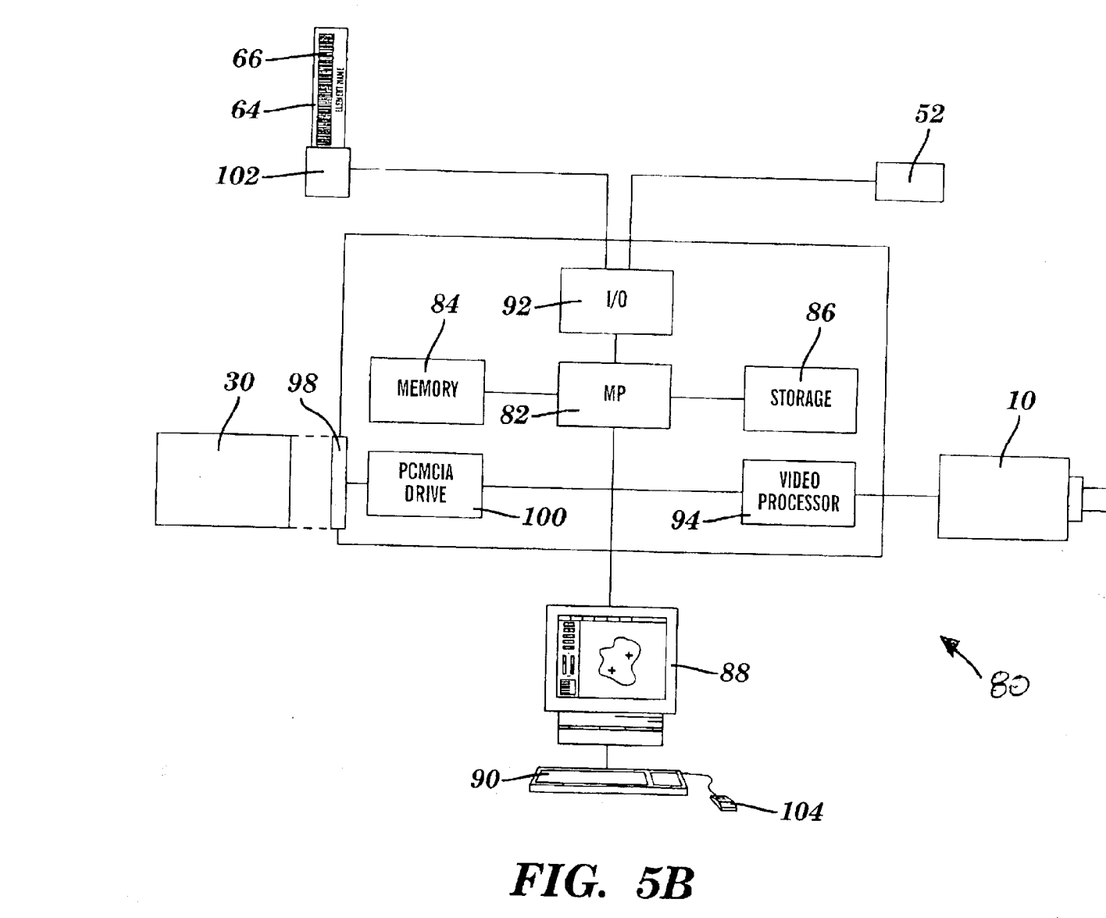
FIG. 5B illustrates a schematic overview of a base computer system according to a preferred embodiment of the present invention.

In another aspect of a preferred embodiment of the present invention, a master database program may be stored and operated on a base computer 80, shown in FIGS. 5A and 5B. The camera 10 or the memory module 30 may be interconnected with the base computer 80 before and after a thermographic survey is performed to transfer survey data to and from the camera 10 or memory module 30. In this case the base computer 80, which may also be a portable or laptop computer and which may be taken to a survey sight by an operator, includes a digital data processor 82, an internal memory 84, a data storage device 86, a display device 88, a data entry keyboard 90, a mouse 104 and an I/O, terminal 92 for interconnecting the base computer 80 with other devices. The base computer 80 may also include a video processing module 94 for directly connecting with the camera 10 and for receiving digital or analog image and other data from the camera 10 and for further processing image and other data using program instructions controlled by the processor 82

The computer 80 preferably also includes a PCMCIA memory card slot 98 for receiving the memory card 30 therein, after removal from the camera 10, and a PCMCIA memory driver 100 for interfacing between the processor 82 and the memory module 30. Note that other memory slots and memory drivers may also be employed without deviating from the intended scope of the present invention. The base computer 80 may also include a barcode scanner 52 attached to the I/O port 92 and interfacing with the processor 82 so that bar-codes may also be scanned and stored in the memory 84. In addition, the base computer 80 includes a barcode printer 102 attached to the I/O port 92 and interfacing with the processor 82 so that bar-codes 66 may be printed onto a barcode label 64.

The base computer 80 includes a number of programs stored in the memory 84 or in the storage device 86 and operating to control the computer system 80 and to interface with the camera 10, the keyboard 90, the display device 88, the barcode scanner 52, the barcode printer 102 and any other device which may be interconnected therewith through the I/O ports 92 or otherwise. These programs may include an operating system, e.g. Windows 95 or NT, MAC OS, UNIX, or the like, as well as application programs and interface drivers. In addition a standard or customized database application program specifically configured for storing and organizing thermographic survey data is also preferably installed on the base computer 80 and operated by the processor 82.

Figure 6A:
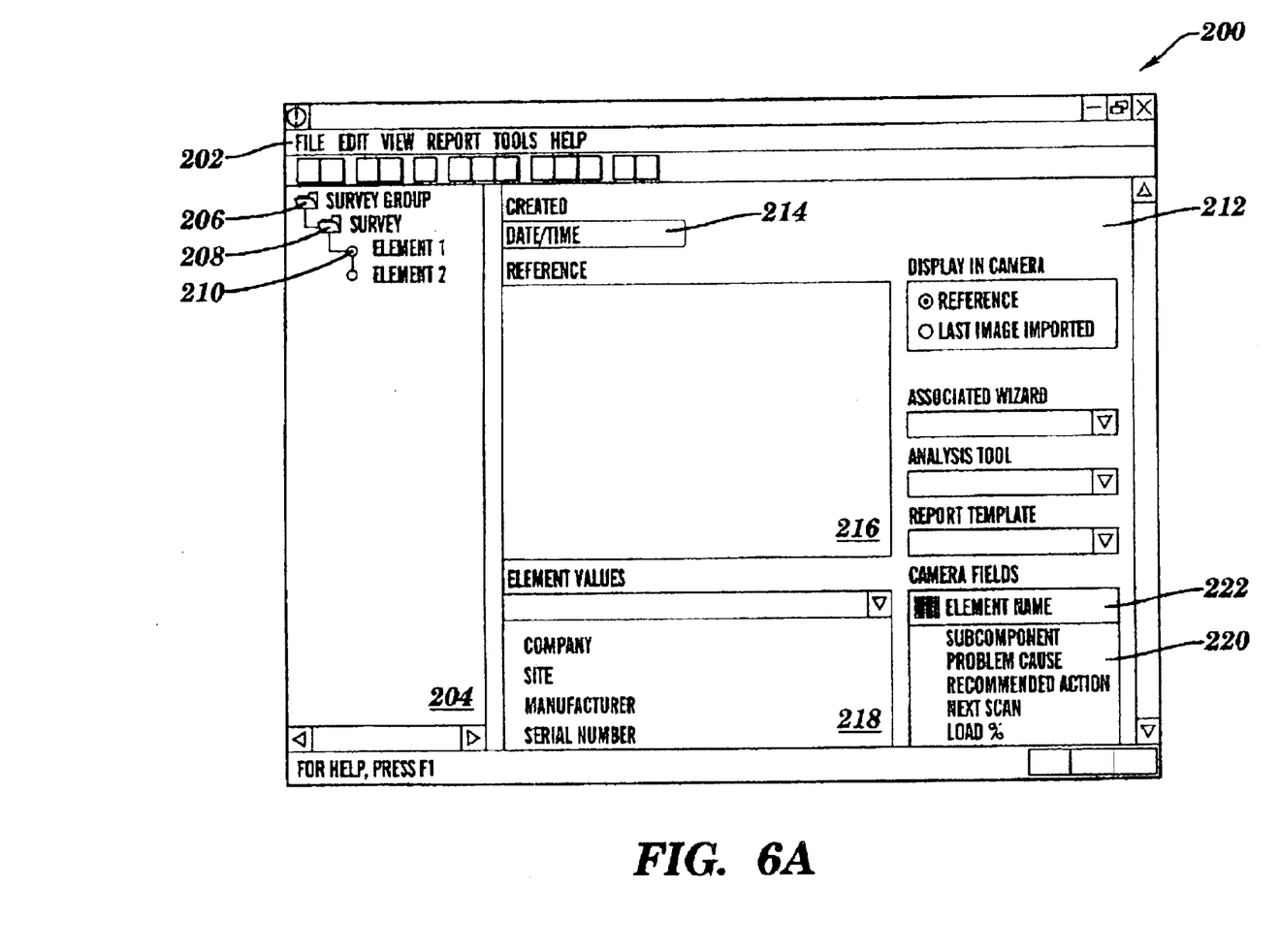
FIG. 6A illustrates a graphical user interface screen shot displayed by the base computer system according to a preferred embodiment of the present invention.
Figure 6B:
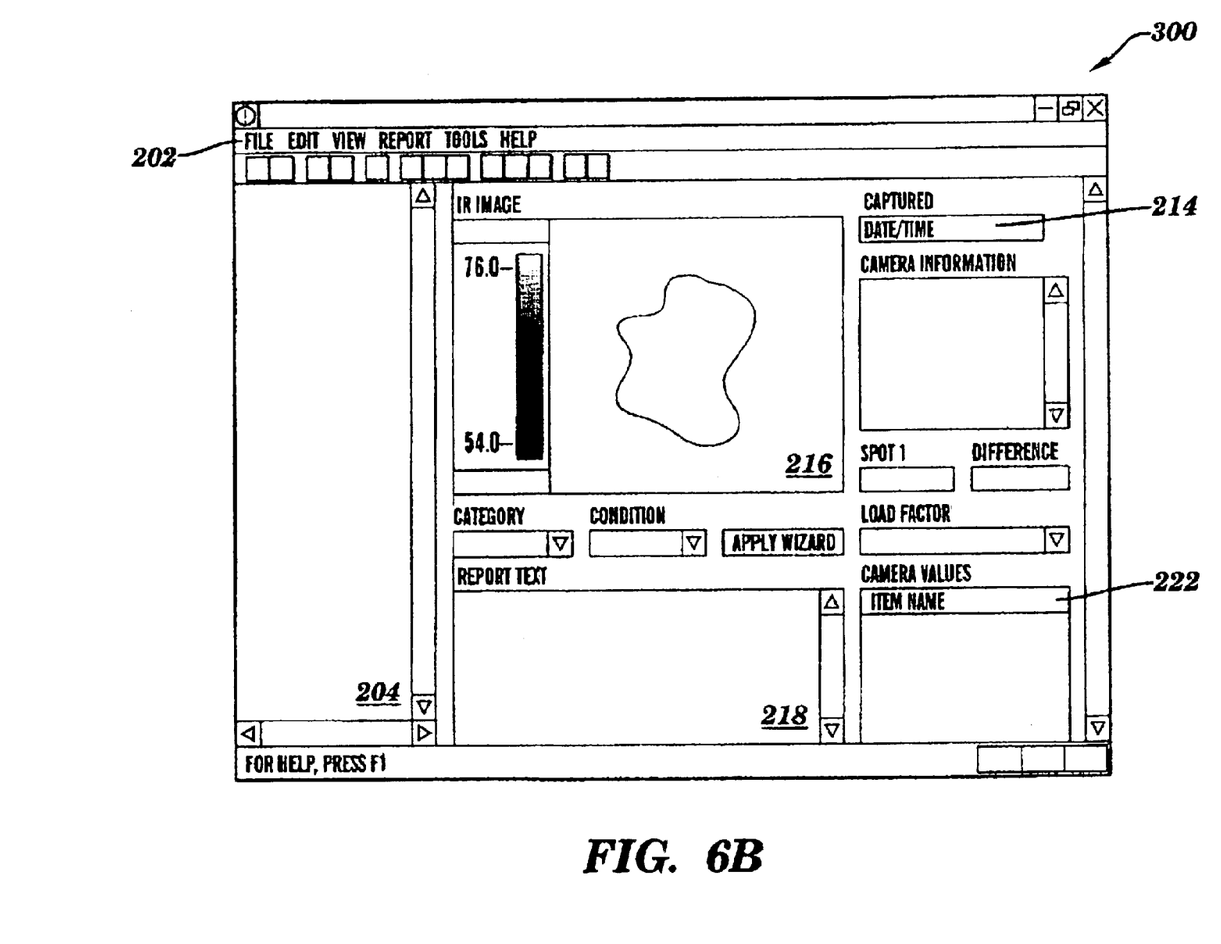
FIG. 6B illustrates an other embodiment of a graphical user interface screen shot displayed by the base computer system according to a preferred embodiment of the present invention.

The database program may include a number of data display layouts, e.g. 200 and 300 illustrated in FIGS. 6A and 6B. The display layouts 200 and 300 provide a graphical user interface to the database program so that an operator may view, organize, edit, search or create reports based on thermographic survey data. Moreover, an operator can add or delete survey elements to a survey, create a new survey, create or edit a survey schedule, create an archive file or perform digital processing on survey element image files to further analyze the survey data.

The display layouts 200 and 300 shown in FIGS. 6A and 6B as might be displayed on the display device 88 include a tool menus 202 for displaying various pull down menus which can be selected by an operator using the keyboard 90 or mouse 104. A directory and file window 204 displays directories and files by name for ease of organizing thermographic survey data into groups or directories. A survey group directory 206 may include a plurality of thermographic surveys organized by survey directories 208. Each survey directory 208 may include survey element records 210.

Each element record 210 includes many data fields associated with a particular survey element and stored in the memory 84. The data fields which may be video clips, still video images, alphanumeric or graphical fields, audio fields or fields which perform special functions such as calculations, automatic data entry or image processing are displayed on a display layout 200 or 300 in record windows, referred to generally by reference numeral 212. In FIGS. 6A and 6B record windows 200 include a date and time field 214. Image windows 216 display images of the survey element. The images may be either still or video clip images which may show an infrared image or a visible image of the survey element and which may be a reference image of the survey element or an image recorded during a recent survey. Other data fields may include element value fields 218 which may include information about the survey element, e.g. the location of the element, the element manufacturer and installation date, serial numbers or other information as may be required by an operator to analyze the results of a survey. Another data field group includes camera fields 220 which include data relating to the conditions under which the image was recorded as well as trouble shooting steps, e.g. camera settings, survey element load and ambient environmental conditions at the time the survey image was recorded, survey schedules, problem causes, recommended actions and other data fields associated with capturing an image of the survey element.

An element identifying field 222 is provided, on each display layout 200 and 300, which uniquely identifies a survey element. The element identifying field 222 may comprise an alphanumeric name or title of the survey element which may also be used to name the survey element record 210 so that the survey element is easily identified. In particular, in accordance with a preferred embodiment of the present invention, the element identifying field 222 is converted to a barcode using a barcode alpha-numeric conversion program, e.g. CODE 39, which is well known. In this case the application program CODE 39 is loaded onto the base computer 80 such that if an element identifying field 222 is created or modified, a barcode 66 may be created by the CODE 39 program and saved in a separate database field. CODE 39 is a barcode application used in many industrial applications which converts a small subset of the ASCII characters set to a barcode symbol. In this case the upper case letters A through Z, the numbers 0 through 9 and the symbols *$/+% plus a space may be converted to a barcode symbol. If an operator chooses an element identifying name or if an older element identifying name includes lower case letters or other symbols not supported by CODE 39, the characters will be bar-coded by CODE 39 as follows.

Promote all lower case letters to upper case.

Replace all characters that are not supported by CODE 39 with a period (.).

Replace all spaces with a period (.).

In addition, the * character is usually inserted at the beginning and end of a barcode. These steps may be done automatically by the barcode converting program or another program or by an operator or by an automatic entry feature of the database program. Consequently, a survey element named "Scrubber #7" would be converted to "*SCRUBBER . . . 7*" by CODE 39 prior to storing the converted element name in the barcode label field which will be used as the element identifying barcode 66.

The barcode 66 may also be printed onto a label 64, e.g. having an adhesive backing, by the barcode printer 102. The thermographer may then take a barcode label 64 to the survey element in the field and attach the label 66 to the survey element or onto an associated name plate or onto a surface near the survey element. Since the barcode 66 uniquely identifies the survey element, the barcode scanner 52 attached to the camera 10 may be used to scan the barcode label associated with the survey element such that the survey element is uniquely identified to the camera processor 48. The camera processor 48 may then upload only the data needed for recording an image of the uniquely identified survey element from the memory module 30. In addition, the survey element image recorded by the camera 10 will be uniquely associated with the element identifying name of the barcode 66 scanned by the barcode scanner 52.

Thus the integrated infrared camera 10 of the present invention provides a mobile thermographic survey device capable of easy portability from one thermographic survey element to another without the need for a mobile cart or other cumbersome equipment. Moreover, the barcode label 64 associated with each survey element provides an identifying feature which when scanned by the bar code scanner 52 uniquely identifies the survey element to the video camera system so that a video image of the survey element will be stored in an appropriate memory field of the survey database.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications, e.g. an infrared sensor assembly and an infrared video camera system, those skilled in the art will recognize that its usefulness is not limited thereto and that the present invention can be beneficially utilized in any number of environments and implementations including but not limited to video surveying and or archiving of art objects or other collectibles, for tracking video images of real estate properties, capital equipment, patient medical images or the like or in any other video image storage requirement wherein video images of elements are periodically updated. Accordingly, the claims set forth below should be construed in view of the full breadth and spirit of the invention as disclosed herein.

What we claim and desire to secure by Letters of Patent of the United States are the following:

1. A method for capturing a video image of an element comprising the steps of:

(a) providing a video camera system comprising a digital data processor, a video data capturing system and a memory module each housed within a camera body;

(b) storing a predetermined identifying name of the element in the memory module;

(c) associating a barcode with the element, said barcode comprising a bar pattern representative of the predetermined identifying name of the element;

(d) scanning the barcode with a barcode scanner directly connected to the video camera system by a port in the camera body thereby generating an electrical signal in response to scanning the bar pattern;

(e) interpreting the electrical signal within the video camera system to identify the element to the video camera system;

(f) capturing the video image of the element with the video data capturing system;

(g) processing the video image of the element with the digital data processor to provide a digital video image of the element; and, (h) storing the digital video image of the element in the memory module with the identifying name of the element associated therewith.

2. The method according to claim 1 wherein the step of storing the predetermined identifying name of the element further comprises the step of:
   (a) establishing an element record, on the memory module, said element record at least comprising a first data field for storing the identifying name therein, and, a second data field for storing the digital video image therein and wherein each data field of the element record is associated with the identifying name of the element.

3. The method according to claim 2 wherein the element record further includes a plurality of other digital data fields for storing other digital data relating to the element.

4. The method according to claim 3 wherein the step of storing a predetermined identifying name of the element further comprises the step of storing the other digital data relating to the element in said other digital data fields.

5. The method according to claim 4 wherein the video camera system includes a display device, further comprising the step of:
   (a) displaying the identifying name of the element on the display device in response to interpreting the electrical signal; and,
   (b) displaying selected of said other digital data stored in the element record on the display device in response to interpreting the electrical signal.

6. The method of claim 3 further comprising the steps of:
   (a) determining parameters relating to conditions of capturing of the video image of the element; and,
   (b) storing the parameters in said element record.

7. The method of claim 1 further comprising the steps of:
   (a) determining parameters relating to conditions relating to the capturing of the video image of the element;
   (b) storing the parameters in the memory module; and,
   (c) associating the parameters with the identifying name of the element.

8. The method according to claim 1 wherein the memory module comprises a removable memory module installed into a memory module port of the video camera system and wherein the step of storing the digital video image of the element in the memory module stores the digital video image in the removable memory module.

9. The method according to claim 8 wherein the removable memory module comprises a PCMCIA card installed in a PCMCIA slot of the video camera system.

10. The method according to claim 1 wherein the element comprises a plurality of elements and wherein each of the plurality of elements has a predetermined identifying name and a barcode comprising a bar pattern representative of the predetermined identifying name associated therewith; and further wherein the step of storing the predetermined identifying name of the element in the memory module is repeated for each of the plurality of elements, further comprising the steps of;
   (a) selecting any one of the plurality of elements in any order; and,
   (b) repeating steps c–g, of claim 1, until a video image of up to all of the plurality of elements is stored in the memory module.

11. The method according to claim 1 wherein the video camera system includes a display device driven by the digital data processor further comprising the step of:
   (a) displaying the digital video image of the element on the display device; and, (b) displaying the identifying name associated with the element on the display device simultaneously with displaying the video image of the element.

12. The method of claim 1 wherein the video camera system includes a display device further comprising the step of:
   displaying the identifying name of the element on the display device in response to interpreting the electrical signal.

13. A method for performing a videographic survey of a plurality of elements comprising the steps:
   (a) preparing a videographic survey database on a base computer operating a database program for storing and organizing data, the videographic survey database including a separate element record for each of the survey elements with each separate element record comprising a first data field for storing an identifying name of the survey element and a plurality of other data fields associated with the identifying name for storing other data associated with the survey element, the other data fields including data fields for storing any one of, a video image, an audio image, an audio data file, a text data file and a graphic data file;
   (b) transferring the separate element record for each element of the survey from the base computer to a memory module contained within a video camera system;
   (c) associating a barcode, including a bar pattern representative of the identifying name of the element, with each of the survey elements;
   (d) selecting one of the survey elements of the videographic survey for recording a video image thereof;
   (e) scanning the barcode associated with the selected one of the survey element with a barcode scanner which is in direct communication with the video camera system to determine the identifying name of the selected element, thereby identifying the selected element to the video camera system;
   (f) recalling the element record associated with the selected element from the memory module;
   (g) capturing a video image of the selected element with the video camera system;
   (h) converting the video image to a digital video image within the video camera system; and
   (i) storing the digital video image in an appropriate data field of the element record.

14. The method according to claim 13 wherein the step of preparing a videographic survey database further comprises the steps of:
   (a) converting the identifying name of the element to a barcode pattern using program steps stored on the base computer;
   (b) printing the barcode pattern representing the identifying name of the element onto a barcode label using a printer associated with the base computer; and,
   (c) locating the barcode label at a location associated with the element.

15. The method according to claim 13 wherein the step of transferring the separate element record for each element of the survey from the base computer to a memory module contained within the video camera system further comprises the steps of one of:
   (a) connecting the video camera system with the base computer by an interface cable and transferring the element record from the base computer to the memory module contained with the video camera system via the interface cable; and,
   (b) removing a removable memory module from a memory port provided in the video camera system and installing the removable memory module into a memory port provided on the base computer;

(c) transferring the element record from the base computer to the removable memory module; and, (d) thereafter returning the removable memory module to the video camera system.

16. A videographic survey system for capturing an image of a plurality of survey elements comprising:

(a) a base computer for preparing a videographic survey database;

(b) a database program operating on the base computer for creating a separate element record for each survey element with each separate element record comprising an identifying name data field for storing an identifying name of the survey element therein and a plurality of other data fields associated with the identifying name data field for storing other data associated with the survey element;

(c) a video camera system for capturing a video image of a selected survey element;

(d) means for transferring the separate element record for each survey element from the base computer to a memory module contained within the video camera system;

(e) a plurality of barcode labels associated one with each of the plurality of survey elements of the videographic survey, each barcode label including a bar pattern representative of the identifying name of the survey element associated therewith;

(f) a barcode scanner in direct communication with the video camera system for scanning the barcode label associated with the selected survey element to identify the selected survey element to the video camera system; and, (g) a digital data processor contained within the video camera system for storing the video image of the selected survey element onto the memory module with the identifying name of the selected survey element associated therewith in response to capturing the video image.

17. The videographic survey system of claim 16 further comprising:

(a) barcode converting program steps stored on the base computer for converting each of the element identifying names to a bar pattern representing the element identifying name; and, (b) a printer associated with the base computer for printing the barcode labels for associating with the survey elements.

18. The videographic survey system according to claim 16 wherein said means for transferring separate element records to the memory module associated with the video camera system comprises one of:

(a) an interface cable connected between the base computer and the video camera system for transferring the element records from the base computer to the memory module associated with the video camera system via the interface cable; and, (b) a removable memory module which is movable between a memory port of the video camera system and a memory port of the base computer for interfacing with the removable memory module for transferring the element records from the base computer to the removable memory module and thereafter returning the removable memory module to the video camera system.

19. The videographic system according to claim 18 wherein the removable memory module comprises a PCMCIA card.

20. An integrated video camera system for capturing a video image of a selected videographic survey element having a unique identifying name comprising;

(a) a video image capturing system for capturing the video image of the selected element, (b) a digital data processor for controlling the video image capturing system;

(c) an analog to digital conversion module for converting the analog video image to a digital video image;

(d) a camera memory module in communication with the digital data processor for storing the unique identifying name of the selected element as well as for providing memory space for storing other data associated with the selected element in data fields, said other data having the identifying name of the selected element associated therewith;

(e) a barcode scanner, in communication with the digital data processor for generating an electrical signal in response to scanning a barcode label associated with the selected element, said barcode label having a bar pattern representing the unique identifying name printed thereon;

(f) a first set of program steps stored on the camera memory module and executable by the digital data processor for interpreting the electrical signal generated by the barcode scanner and for recalling data fields associated with the selected element from the camera memory module; and, (g) a display device associated with the video camera system and driven by the data processor for displaying the identifying name of the selected element in response to interpreting the electrical signal generated by the barcode scanner.

21. An integrated video camera system according to claim 20, further comprising a camera body for housing the video image capturing system, the analog to digital conversion device, the digital data processor, the camera memory module and the display device therein.

22. An integrated video camera system according to claim 21 further comprising a data entry device housed within the camera body and in communication with the digital data processor for providing an operator interface to the video camera system for selecting various modes of operation of the video camera system by the operator.

23. An integrated video camera system according to claim 21 wherein the display device is viewable by an operator through a viewfinder eyepiece connected to the camera body.

24. An integrated video camera system according to claim 20 wherein the camera memory module comprises two separate memory modules and wherein a first of the two memory modules remains within the camera body and wherein a second of the two memory modules is removable from the camera body for transferring video image captured by the camera system to another device.

25. An integrated video camera system according to claim 20 further comprising a second set of program steps stored on the camera memory module and executable by the digital data processor for storing a video image of the element onto the camera memory module with the element name associated therewith.

26. An integrated video camera system according to claim 20 wherein the video image capturing system comprises an infrared sensor assembly for providing an electrical signal in response to receiving thermal radiation emitted by the selected element.

27. A system for conducting a videographic survey which requires capturing a video image of each a plurality of survey elements and wherein each survey element has a unique identifying name associated therewith comprising:
  (a) a base computer for operating a master database program used for storing and organizing data relating to each of the survey elements;
  (b) a separate element record of the master database program for each of the survey elements, the separate element record comprising an identifying name data field and a plurality of other data fields associated with the identifying name data field, said plurality of other data fields including data fields for storing any one of a video image, an audio data file, a text data file and a graphics data file;
  (c) a video camera system for capturing the video image of each of the plurality of survey elements, the video camera system including a memory device for receiving element records of the master database program from the base computer and for storing video images captured by the video camera system with an appropriate identifying name field associated therewith;
  (d) a barcode scanner in communication with the video camera system for scanning a barcode label associated with each of the plurality of survey elements and wherein the barcode labels include a bar pattern representative of the identifying name of the survey element printed thereon; and,
  (e) a barcode interpreting program loaded onto the video camera system for interpreting the barcode pattern, to identify the element name to the video camera system so that the video image of the element can be stored in the memory with the appropriate element name associated therewith.

28. The system according to claim 27 wherein the memory device is removable from the video camera system and installable in the base computer for transferring data between the memory device and the base computer.

29. The system according to claim 27 wherein the video camera system further comprises:
  (a) a display device; and,
  (b) a processor for driving the display device to display a display layout comprising a field for displaying the identifying name of the selected survey element in response to scanning the barcode associated with the selected survey element and a field for displaying a video image of the selected survey element.

30. The system according to claim 27 further comprising:
  (a) a program operating on the base computer for convening elements names to a bar pattern; and,
  (b) a printer associated with the base computer for printing the bar patterns onto labels for associating with survey elements.

31. The system according to claim 27 wherein the video camera system further comprises an infrared sensor assembly for providing an electrical signal in response to receiving thermal radiation emitted by each of the plurality of survey elements.

32. A method for capturing a video image of an element comprising the steps of;
  (a) providing a video camera system comprising a digital data processor, a video data capturing system and a memory module each housed within a camera body;
  (b) storing a predetermined identifying name of the element in the memory module;
  (c) scanning a barcode associated with the element with a barcode scanner directly connected to the video camera system by a port in the camera body, said barcode including a bar pattern representative of the predetermined name of the element; and,
  (d) displaying the predetermined element name on a display device of the video camera system in response to scanning the barcode, thereby identifying the element to an operator of the video camera system.

33. The method of claim 32 further comprising the steps of:
  (a) capturing the video image of the element with the video data capturing system; and,
  (b) storing the video image of the element in the memory module with the predetermined element name associated therewith.

34. The method of claim 32 further comprising the step of: simultaneously displaying the predetermined element name and the captured video image of the element on the display device.

35. The method of claim 32 further comprising the steps of:
  (a) storing a plurality of data fields relating to the element in the memory module, each data field having the predetermined element name associated therewith; and,
  (b) displaying at least a portion of the plurality of data fields relating to the element on the display device in response to scanning the barcode, thereby providing the operator with access to the data in the data fields.

36. The method of claim 35 further comprising the steps of:
  (a) capturing the video image of the element with the video data capturing system;
  (b) storing the video image of the element in the memory device with the predetermined element name associated therewith, and,
  (c) storing additional data relating to the capturing of the video image in the memory device with the predetermined element name associated therewith.

37. A method for capturing a video image of an element comprising the steps of;
  (a) providing a video camera system which houses a memory module, a digital data processor and a video image capturing system within a camera body thereof and which include a barcode scanner in communication the digital data processor for scanning barcode patterns;
  (b) storing a predetermined identifying name for each of a plurality of elements in the memory module; and,
  (c) scanning a barcode associated with any one of the plurality of elements with the barcode scanner to identify the element to the digital data processor, said barcode including a bar pattern representative of the predetermined identifying name.

38. The method of claim 37 further comprising the steps of:
  (a) capturing an image of the element with the video data capturing system; and,
  (b) storing the image of the element in the memory module with the predetermined identifying name of the element associated therewith.

39. A video camera system comprising:
  (a) a digital data processor, a video data capturing system and a memory module housed within a camera body for capturing, processing and storing videographic images; and,
  (b) a barcode scanner in communication the digital data processor for scanning barcode patterns for identifying elements to be videographed to the digital data processor.

40. The video camera system of claim 39 wherein the video data capturing system comprises an infrared sensor assembly for providing an electrical signal in response to receiving thermal radiation emitted by the elements.

* * * * *